United States Patent [19]

Fujikura et al.

[11] 4,374,052
[45] Feb. 15, 1983

[54] PERFUME COMPOSITION

[75] Inventors: Yoshiaki Fujikura, Tochigi; Yoshiaki Inamoto; Naotake Takaishi, both of Utsunomiya; Motoki Nakajima, Saitama, all of Japan

[73] Assignee: Kao Corporation, Tokyo, Japan

[21] Appl. No.: 241,855

[22] Filed: Mar. 9, 1981

[30] Foreign Application Priority Data

Mar. 14, 1980 [JP] Japan ................................. 55-32435
Dec. 10, 1980 [JP] Japan ............................... 55-174247

[51] Int. Cl.$^3$ ............................................... A61K 7/46
[52] U.S. Cl. ............................ 252/522 R; 252/174.11
[58] Field of Search .................................... 252/522 R

[56] References Cited

U.S. PATENT DOCUMENTS 4,123,394 10/1978 Skorianetz et al. ............. 252/522 R
4,275,251 6/1981 Sprecker et al. .................... 568/817

FOREIGN PATENT DOCUMENTS 2000122 1/1979 United Kingdom ................ 560/117

OTHER PUBLICATIONS

*Survey of Organic Synthesis*, New York, 1970, p. 818, No. 11.
Koch et al., Ann. 638, 111, (1960).
Fieser et al., *Reagents for Organic Synthesis*, vol. 4, p. 189, (1974).

*Primary Examiner*—John F. Niebling
*Attorney, Agent, or Firm*—Birch, Stewart, Kolasch & Birch

[57] ABSTRACT

Use of the compound methyl tricyclo[5.2.1.0$^{2,6}$]decane-2-carboxylate in a perfume composition provides a herbal note or essence to the composition.

4 Claims, No Drawings

PERFUME COMPOSITION

BACKGROUND OF THE INVENTION

The present invention relates to perfume compositions containing a tricyclodecane carboxylic acid ester and to a process for producing the same.

The present inventors have been interested in the fact that among the terpene compounds, many of those having polycyclic structures have excellent fragrances. The inventors have synthesized numerous compounds having polycyclic structures and have examined the fragrances thereof.

SUMMARY OF THE INVENTION

A primary object of the present invention is to provide a perfume composition which is stable for a long period of time, even under severe conditions.

Another object of the present invention is to provide methods for producing essential compounds useful as an ingredient of perfume compositions.

These and other objects and advantages of the present invention may be accomplished by the compounds of the following formula (I). Thus, in accordance with the present invention, it has been found that methyl tricyclo[5.5.1.0$^{2,6}$]decane-2-carboxylates of the following formula (I) have excellent fragrances and high thermal stabilities and quite high stabilities to acidic or alkaline conditions and that they do not become colored or denatured over a long period of time.

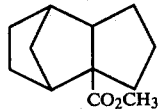
(I)

DESCRIPTION OF THE PREFERRED EMBODIMENTS

The fragrance of tricyclic carboxylates of the formula (I) may be classified roughly as a herbal odor.

The compounds of formula (I) have two isomers as shown formulae (I-x) and I-n):

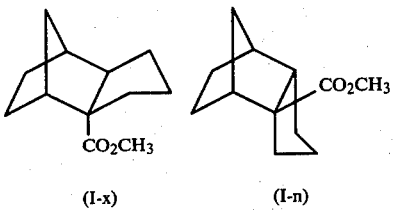

The isomer of formula (I-x)(exo-trimethylene compound) has a fragrance that is slightly different from the other isomer of formula (I-n)(endo-trimethylene compound). More particularly, the former compound has a piney-green-herbal odor and the latter compound has a camphoraceous-minty-herbal odor.

The compounds of formula (I) have been known as interesting compounds in synthetic chemistry (H. Koch and W. Haaf, Ann. 638, 111 (1960)) or as an intermediate for the production of antiviral agents (Japanese Laid Open Patent Application No. 53-82765(1978)). However, it is to be noted that although these compounds have been known as an intermediate of antiviral agents, no ideas of using the same as a perfume component have been proposed. The present inventors found that these methyl esters have an excellent herbal fragrance and are very stable even at an elevated temperature or under acidic or alkaline conditions and that they are not colored or denatured over a long period of time.

Generally, when perfumes are incorporated in acidic or alkaline detergents, they are exposed to severe conditions such as pH 1-4 or pH 10-13, respectively, and as the temperature is elevated, their smells often are altered or degraded. However, the tricyclic carboxylic acid esters of the present invention are stable and free of such phenomena.

As a matter of course, the tricyclic carboxylic acid esters of the present invention may be incorporated to afford a herbal note in products in which perfume materials are generally used such as perfumes, soaps, shampoos, hair rinses, detergents, cosmetics, floor waxes, sprays, and aromatics, in addition to acidic and alkaline detergents.

Structurally, the tricyclic carboxylic acid esters of the present invention are esterification products of the acids (II) with methanol. However, it has been found that the reaction hardly proceeds when the free acid is directly esterified with the alcohol under conventional reaction conditions. It is advantageous that free acid (II) be first converted into acid halide (III) and then acid halide (III) reacted with an alcohol to form ester (I).

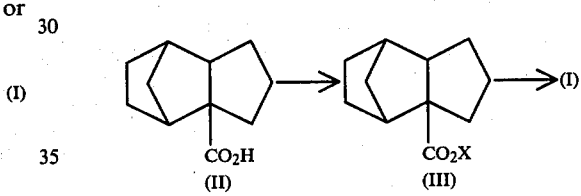

Acid halide (III) may be obtained by reacting free acid (II) with a halogenating agent such as thionyl chloride, phosphorus trichloride, phosphorus pentachloride, thionyl bromide, phosphorus tribromide or phosphorus pentabromide by an ordinary process. For obtaining ester (I), the acid halide (III) thus formed is reacted with methanol. The reaction proceeds generally at room temperature without any heating.

Another process wherein free acid (II) is reacted with an esterifying agent such as dimethyl sulfate to form ester (I) may be employed in place of the above process.

Any lower alcohols, for example, methanol, ethanol and i-propanol may be used as the reaction medium to form esters with dimethyl sulfate. In this process, no alkaline or acid catalyst is needed.

The present inventors have further found that if the carboxylic acid (II) is reacted with dimethyl sulfate in the presence of an aqueous alkali solution without using any solvent such as acetone or lower alcohols, the ester (I) can be obtained in a high yield without any difficulty in stirring the reaction system during the reaction. In addition, the after-treatment can be effected easily because of the absence of an organic solvent and the fact that by-products are formed in only an extremely small amount.

As the aqueous alkali solution used in the above process, there may be mentioned alkali metal hydroxides and alkali metal carbonates in an aqueous solution. As the alkali metals, sodium and potassium are most suitable. The aqueous alkali solution may be a 5-50% solution of the above alkali substance, preferably a 10-30% solution thereof. Dimethyl sulfate may be used in an amount of 1.0–2.0 moles, particularly about 1.0–1.4 moles, per mole of the carboxylic acid (II). The alkali substance may be used in an amount of at least 1 mole, suitably 1.0–1.5 moles and most preferably about 1.0–1.2 moles, per mole of the carboxylic acid.

The reaction is preferably carried out by adding an aqueous alkali solution dropwise to a solution of a mixture of carboxylic acid (II) and the dimethyl sulfate. It has been found that the yield of the carboxylic acid ester can be increased by adding the aqueous alkali solution in at least two portions and that after the addition of a portion thereof, allowing the mixture to react for a proper period of time and then taking out the aqueous layer, this operation being repeated at least two times. A reason therefor is considered to be as follows. Water in the reaction system plays a role of dissolving the alkali substance and the alkali metal salt of monomethyl sulfate formed. Further, the water inhibits the improvement in yield of the product, since it decomposes the reactant dimethyl sulfate. If the water is properly removed from the reaction system, the decomposition of dimethyl sulfate can be prevented. The number of times of addition of the portions of aqueous alkali solution is suitably up to about 10, since if the number of times of addition is excessive, the operation becomes too complicated, though the yield is improved as the number is increased. Alternatively, the aqueous alkali solution may be added not in portions but dropwise continuously and only the aqueous layer is taken out continuously. For example, if the aqueous alkali solution is added at once in the case that 1.1 moles of dimethyl sulfate and 1.1 moles of sodium hydroxide are used per mole of the carboxylic acid (II) as shown in the following example, the per-pass yield (after the purification) of the methyl carboxylate is 80%, whereas in case the aqueous alkali solution is added in two portions, the per-pass yield is 91% and in case said solution is added in four portions the per-pass yield is 92.5%.

The thus prepared methyl tricyclodecane carboxylate of the present invention may be incorporated as an ingredient of a perfume composition in other perfumed materials in order to modify the fragrance of the composition as having a herbal note.

The free acid (II) used as the starting material is obtained by (A) a process wherein water is added to dicyclopentadiene (VI) in the presence of an acid catalyst to form a hydrate followed by hydrogenation and then the hydrate is subjected to a Koch carboxylation reaction or (B) a process wherein one of the two unsaturated bonds of dicyclopentadiene is hydrogenated and then it is subjected to the Koch carboxylation reaction:

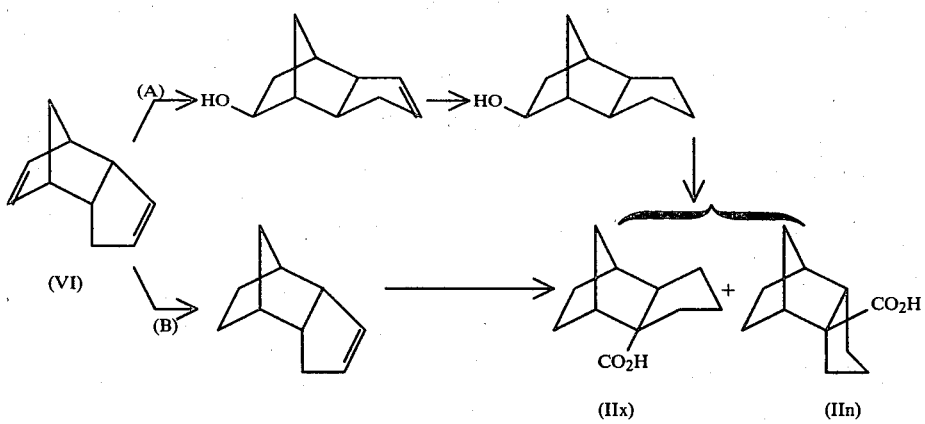

By either process (A) or (B), the resulting free acid is a mixture of exo-trimethylene compound (II-x) and endo-trimethylene compound (II-n). The ratio of (II-x) to (II-n) is generally 1:1, but it varies depending on the conditions.

The free acid mixture may be esterified directly by the above described process without the separation of the mixture into the respective components, thereby forming the ester which may directly be used as a perfume material.

In case either the exo-trimethylene ester (I-x) or endo-trimethylene ester (I-n) is to be obtained alone or a mixture thereof containing either (I-x) or (I-n) in a larger amount, a process wherein the mixture of the esters is divided into the respective components by precision distillation may be employed.

The following examples further illustrate the present invention, which by no means should be regarded as a limitation of the present invention.

EXAMPLE 1

110 g (0.55 mole) of sodium hydroxide in a 20% aqueous solution was added dropwise to a mixture of 90.0 g (0.50 mole) of tricyclo[5.2.1.0$^{2,6}$]decane-2-carboxylic acids (mixture of endo- and exo-compounds) and 69.3 g (0.55 mole) of dimethyl sulfate over 2 hours under stirring at 50° C. After completion of the addition, stirring was continued at that temperature for 30 minutes. Then, 16.5 g (0.0825 mole) of 20% aqueous sodium hydroxide solution was added thereto and the whole mixture was stirred at 100° C. for 45 minutes, in order to decompose unreacted dimethyl sulfate. After completion of the decomposition, the mixture was allowed to stand at room temperature for a while to form layers. The organic layer was separated. By distillation, 77.5 g (yield 80%) of pure methyl tricyclo[5.2.1.0$^{2,6}$]decane-2-carboxylate was obtained. It was revealed by fractional distillation that the product was a mixture of methyl exo-tricyclo[5.2.1.0$^{2,6}$]decane-endo-2-carboxylate and methyl endo-tricyclo[5.2.1.0$^{2,6}$]decane-exo-2-carboxylate.

EXAMPLE 2

55.0 g (0.275 mole) of a 20% aqueous sodium hydroxide solution was added dropwise to a mixture of 90.0 g (0.5 mole) of tricyclo[5.2.1.0$^{2,6}$]decane-2-carboxylic acid (mixture of endo- and exo-compounds) and 69.3 g (0.55 mole) of dimethyl sulfate over one hour under stirring at 50° C. After completion of the addition, stirring was continued at that temperature for 30 minutes. After completion of the stirring, the mixture was allowed to stand at room temperature for a while to form layers. The lower aqueous layer was taken out. The temperature was elevated again to 50° C. 55.0 g (0.275 mole) of sodium hydroxide in a 20% aqueous solution was added dropwise to the remainder over one hour under stirring at 50° C. After completion of the addition, the mixture was stirred at that temperature for 30 minutes. Then, 16.5 g (0.0825 mole) of a 20% aqueous sodium hydroxide solution was added thereto and the whole mixture was stirred at 100° C. for 45 minutes in order to decompose unreacted dimethyl sulfate. The mixture was allowed to cool and divided into layers. After the distillation, 88.3 g (yield 91.0%) of pure methyl tricyclo[5.2.1.0$^{2,6}$]decane-2-carboxylate was obtained.

EXAMPLE 3

110 g (0.55 mole) of sodium hydroxide in a 20% aqueous solution was added dropwise dividedly in 4 portions to 90.0 g (0.5 mole) of the same carboxylic acid as used in Example 2 and treated in the same manner as in Example 2 to obtain 89.7 g (yield 92.5%) of pure methyl tricyclo[5.2.1.0$^{2,6}$]decane-2-carboxylate.

EXAMPLE 4

A floral fragrance composition for detergents was prepared with the following composition:

| | |
|---|---|
| β-Phenethyl alcohol | 200 |
| p-5-Butyl-α-methylhydrocinnamic aldehyde | 40 |
| Linalool | 50 |
| γ-Methylionone | 40 |
| Menthanyl acetate | 20 |
| α-Hexylcinnamic aldehyde | 200 |
| Benzyl salicylate | 40 |
| Styraryl acetate | 20 |
| Terpineol | 40 |
| Patchouli oil | 10 |
| Geranium oil | 20 |
| Cedryl acetate | 50 |
| Benzyl acetate | 60 |
| Musk ambrette | 20 |
| Musk Ketone | 20 |
| Coumarin | 20 |
| Geraniol | 50 |
| | 900 |

100 g of methyl tricyclo[5.2.1.0$^{2,6}$]decane-2-carboxylate (an approximately 1:1 mixture of the exo-trimethylene compound and the endo-trimethylene compound) was added to 900 g of the above fragrance composition to obtain a mixed fragrance composition having a slightly increased herbal note or essence.

EXAMPLE 5

0.1% of methyl tricyclo[5.2.1.0$^{2,6}$]decane-2-carboxylate (mixture of exo-trimethylene ester and endo-trimethylene ester in a ratio of approximately 1:1) was added to an acidic detergent of pH 1.5 and an alkaline detergent of pH 10.9. After storage for 20 days, changes in odor were examined to obtain the results shown in the following Table:

| | | Odor Stability | | | |
|---|---|---|---|---|---|
| | | −5° C. | 30° C. | 40° C. | 50° C. |
| Fragrance of the present invention | Acidic detergent (pH 1.5) | O | O | O | O |
| | Alkaline detergent (pH 10.9) | O | O | O | O |
| A generally used fragrance | Acidic detergent (pH 1.5) | O | Δ | x | x |
| | Alkaline detergent (pH 10.9) | O | O | Δ | Δ |

Functional judgment:
O: Stable, no change.
Δ: Some change. The original odor still remains.
x: Unstable. Serious change. The original odor does not remain.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A perfume composition comprising:
    the compound methyl tricyclo[5.2.1.0$^{2,6}$]decane-2-carboxylate of the formula (I):

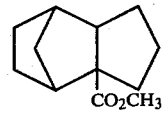

(I)

in an amount sufficient to afford a herbal note or essence to the composition; and an acceptable carrier therefor.

2. A perfume composition according to claim 1, wherein said compound is the endo-trimethylene ester.

3. A perfume composition according to claim 1, wherein said compound is the exo-trimethylene ester.

4. A method of providing a herbal note or essence to a perfume composition, comprising adding the methyl tricyclo[5.2.1.0$^{2,6}$]decane-2-carboxylate of claim 1 in an amount sufficient to provide a herbal note or essence to the composition.

* * * * *